US005270542A

United States Patent [19]

McMurry et al.

[11] Patent Number: 5,270,542

[45] Date of Patent: Dec. 14, 1993

[54] APPARATUS AND METHOD FOR SHAPING AND DETECTING A PARTICLE BEAM

[75] Inventors: Peter H. McMurry; David B. Kittelson; Paul J. Ziemann; Peng Liu, all of Minneapolis, Minn.; Nagaraja P. Rao, Fishkill, N.Y.

[73] Assignee: Regents of the University of Minnesota, Minneapolis, Minn.

[21] Appl. No.: 999,125

[22] Filed: Dec. 31, 1992

[51] Int. Cl.[5] ................ H01J 41/04

[52] U.S. Cl. ................ 250/288; 250/251

[58] Field of Search ................ 250/288, 288 A, 282, 250/251; 55/392; 73/28.04

[56] References Cited

U.S. PATENT DOCUMENTS

| | | | |
|---|---|---|---|
| 3,854,321 | 12/1974 | Dahneke | 73/28 |
| 4,358,302 | 11/1982 | Dahneke | 250/288 |
| 4,863,491 | 9/1989 | Brandt et al. | 250/288 A |

OTHER PUBLICATIONS

*Secondary Electron Emission From Beams of Polystyrene Latex Spheres;* T. D. Hall and W. W. Beeman; Journal of Applied Physics, vol. 47, No. 12., Dec. 1976.

*Aerodynamic Focusing of Particles and Molecules in Seeded Supersonic Jets;* J. Fernandez de la Mora, J. Rosell-Llompart and P. Riesco-Chueca; American Institute of Aeronautics and Astronautics, Inc.; 1989.

*Aerodynamic Focusing of Particles In a Carrier Gas;* J. Fernandez de la Mora and P. Riesco-Chueca; J. Fluid Mech. (1988), vol. 195, pp. 1-12.

*Aerodynamic Focusing of Particles in Incompressible Jets;* N. Rao, J. Navascues and J. Fernandez de la Mora; Apr. 9, 1992.

*High Speed Beams of Small Particles;* Gerhard W. Israel and S. K. Friedlander; Journal of Colloid and Interface Science 24, 330-337 (1967).

*Characteristics of a Capillary-Generated Particle Beam;* Thomas J. Estes, Vincent L. Vilker and Sheldon K. Friedlander; Journal of Colloid and Interface Science, vol. 93, No. 1; May 1983.

*Similarity Theory for Aerosol Beams;* B. Dahneke J. Hoover and Y. S. Cheng; Journal of Colloid and Interface Science, vol. 87, No. 1 May, 1982.

*An Aerosol Beam Spectrometer;* Barton Dahneke and Hermann Flachsbart; Aerosol Science, 1972, vol. 3, pp. 345-349.

*Aerosol Characterization Using Molecular Beam Techniques;* Mayis Seapan, Douglas Selman, Fred Seale, Greg Siebers and Eugene H. Wissler; Journal of Colloid and Interface Science, vol. 87, No. 1, May 1982.

*Measurement of Externally Mixed Sodium Containing Particles In Ambient Air By Single Particle Mass Spectrometry;* C. L. Giggy, S. K. Friedlander and M. P. Sinha; Atmospheric Environment, vol. 23, No. 10, pp. 2223-2229, 1989.

(List continued on next page.)

*Primary Examiner*—Jack I. Berman

*Attorney, Agent, or Firm*—Bell, Seltzer, Park & Gibson

[57] ABSTRACT

A particle beam shaping apparatus preferably includes a prefocusing element and a primary focusing element disposed within a tube. An aerosol beam source having relatively heavy particles and relatively light gas is operably connected to the prefocusing element. The prefocusing element preferentially expands the aerosol beam such that the gas diverges laterally relatively rapidly while the particles diverge laterally relatively slowly. The tube laterally confines the rapidly expanding gas such that the primary focusing element converges the gas upon the particle beam to more narrow the particle beam. A detector may be located downstream of the primary focusing means to sense the particles impinging thereon. A skimmer is preferably interposed between the primary focusing element and the detection means to remove the gas while allowing the particles to pass therethrough. The particles may be electrically charged and deflected prior to their detection such that the particles' relative masses may be determined by the detection means.

38 Claims, 2 Drawing Sheets

OTHER PUBLICATIONS

*Electron-Impact Ionization Time-of-Flight Mass Spectrometer For Molecular Beams;* J. E. Pollars and R. B. Cohen; Rev. Sci. Instru., vol. 58, No. 1, Jan. 1987.

*Mass Spectrometric Analyzer For Individual Aerosol Particles;* Jonathan Allen and Robert K. Gould; Rev. Sci. Instrum., vol. 52, No. 6, Jun. 1981.

*On The Real-Time Measurement of Particles in Air By Direct-Inlet Surface Ace-Ionization Mass Spectrometry;* J. J. Stoffels and C. R. Lagergren; International Journal of Mass Spectrometry and Ion Physics, 40 (1981) 243.

*Particle Analysis by Mass Spectrometry;* M. P. Sinha, C. E. Giffin, Norris, T. J. Estes, V. L. Vilker and S. K. Friedlander; Journal of Colloid and Interface Science, vol. 87, No. 1, May 1982.

*Mass Distribution of Chemical Species in a Polydisperse Aerosol: Measurement of Sodium Chloride in Particles by Mass Spectrometry;* M. P. Shinha and S. K. Friedlander; Journal of Colloid and Interface Science, vol. 112, No. 2, Aug. 1986.

*Properties of Continuum Source Particle Beams I Calculation Methods and Results;* B. E. Dahneke and Y. S. Cheng; J. Aerosol Sci., vol. 10, pp. 257-274 1979.

APPARATUS AND METHOD FOR SHAPING AND DETECTING A PARTICLE BEAM

FIELD OF THE INVENTION

This invention relates to a method and apparatus for shaping and detecting a particle beam, and more particularly to a method and apparatus for shaping and detecting a particle beam utilizing multiple focusing elements.

BACKGROUND OF THE INVENTION

It is often desirable to focus or concentrate particles in a sample environment by forming a particle beam. For example, the detection of the number or presence of particles may employ the formation of a particle beam. Such particle beam formation and subsequent detection is desirable, for example, during microelectronic device processing in which the presence of particles is detrimental to the performance of the resulting microelectronic devices because the particles may deposit on the microelectronic devices' surface and lead to defects which reduce the device yield. By detecting the particles' presence, preventative or corrective measures may be taken to salvage the microelectronic devices.

Several systems have been proposed to focus a particle beam derived from an aerosol in which the particles are suspended in a gas. Such systems typically include a nozzle through which the aerosol is drawn to generate and focus the particle beam. After passing through the nozzle, the gas, whose mass is substantially less than that of the heavier particles, diverges laterally rapidly while the particles may first converge to a focal point prior to slowly diverging laterally. Typical particle beam generation devices direct the beam of slowly diverging particles and rapidly diverging gas to a skimmer having an opening therethrough. The skimmer allows the beam, now consisting of the majority of the particles but only a small fraction of the gas which passed through the nozzle due to the relative rates of divergence of the gas and particles, to pass while redirecting the gas. The particle beam passing through the skimmer generally enters a chamber having a relatively low pressure for detection.

There are three principal types of nozzles utilized to focus aerosol beams. A first such nozzle is a converging conical nozzle such as those described in publications entitled *Properties of Continuum Source Particle Beams* by Dahneke et al., Journal of Aerosol Science, Vol. 10, 1979, pp. 257–274; and *Aerodynamic Focusing of Particles in a Carrier Gas* by Fernandez de la Mora et al., Journal of Fluid Mechanics, Vol. 195, 1988, pp. 1–21. A second type of typical nozzle is a capillary tube such as those disclosed in publications entitled *Mass Distribution of Chemical Species in a Polydisperse Aerosol: Measurement of Sodium Chloride in Particles by Mass Spectrometry* by Sinha et al., Journal of Colloid and Interface Science, Vol. 112, No. 2, August 1986, pp. 573–582; *Particle Analysis by Mass Spectrometry* by Sinha et al., Journal of Colloid and Interface Science, Vol. 87, No. 1, May 1982, pp. 140–153; and *On the Real-Time Measurement of Particles in Air by Direct-Inlet Surface-Ionization Mass Spectrometry,* by Stoffels et al., Vol. 40, 1981, pp. 243–254. A third type of nozzle is a thin plate positioned substantially orthogonal to the longitudinal direction of propagation of the aerosol beam. The thin plate has an orifice therein as described in the publication entitled *Mass Spectrometric Analyzer for Individual Aerosol Particles* by Allen et al., Review of Scientific Instruments, Vol. 52, No. 6, June 1981, pp. 804–809 and *Aerodynamic Focusing of Particles and Molecules in Seeded Supersonic Jets* by Fernandez de la Mora, et al., Rarefied Gas Dynamics: Physical Phenomena, Vol. 117 of *Progress in Astronautics and Aeronautics,* 1989, pp. 247–277.

While all three typical nozzle designs focus the aerosol beam to some extent, the amount of control over the shape of the beam, such as its rate of convergence or divergence or its focal length, is limited. For example, capillary tubes do not produce focused beams and thin plates having an orifice therein produce beams having very short focal lengths which diverge rapidly after passing through the focal point. Furthermore, to the best of the inventors' knowledge, previous investigations of nozzles used to produce particle beams sampled aerosols at pressures ranging from atmospheric to about 20 torr while the particles' diameter was always larger than about 0.1 um.

In order to obtain increased control over the shape of a resultant aerosol beam, nozzles incorporating a capillary tube immediately adjacent to and in contact with a thin plate having an orifice therethrough have been utilized. Such nozzles consisting of a capillary tube and a thin plate having an orifice are described in publications entitled *Measurement of Externally Mixed Sodium Containing Particles in Ambient Air by Single Particle Mass Spectrometry* by Giggy et al., Atmospheric Environment, Vol. 23, No. 10, 1989, pp. 2223–2229; and *Electron-Impact Ionization Time-Of-Flight Mass Spectrometer for Molecular Beams* by Pollard et al., Review of Scientific Instruments, Vol. 58, No. 1, January 1987, pp. 32–37. While the nozzles described in the Giggy and Pollard articles may improve, somewhat, the control over the aerosol beam's shape, the amount of control over the beam's convergence or divergence or its focal length may be limited.

An alternative device to provide increased control over the shape of a particle beam is described in a publication entitled *Aerodynamic Focusing of Particles in Incompressible Jets* by Rao et al., IBM Publication No. IBM-EF-23, Apr. 9, 1992; and U.S. Pat. No. 3,854,321 to Dahneke which issued on Dec. 17, 1974 (hereinafter the '321 patent). As illustrated in FIGS. 1, 3 and 4 of the '321 patent, sheath air is introduced about the aerosol beam, prior to its focusing by the nozzle, to constrain the incident aerosol beam. By using sheath air directed substantially parallel to the flow of the aerosol beam, the aerosol beam, both the particles and the gas, diverges less from its longitudinal axis of propagation. The use of sheath, however, requires a means to produce and to control the flow of the sheath air and adds to the pumping requirements of the system.

Thus, although the formation of particle beams is highly desirable, particularly for use in conjunction with particle detection devices as illustrated in a publication entitled *Secondary Electron Emission From Beams of Polystyrene Latex Spheres* by Hall et al., Journal of Applied Physics, Vol. 47, No. 12, December 1976, pp. 5222–5225, to the best of the inventors' knowledge the art has not heretofore suggested a viable method and apparatus for providing adequate control over the shape and focal length of a particle beam, particularly at relatively low pressures and for relatively small particles. In particular, to the best of the inventors' knowledge, prior particle beam generation devices which produced particle beams of a known and controlled shape were not used to produce particle beams from aerosol sources having pressures less than 20 torr and particles smaller than 0.1 um in diameter.

SUMMARY OF THE INVENTION

Is therefore an object of the invention to provide an improved method and apparatus for shaping a particle beam.

It is another object of the invention to provide an improved method and apparatus for shaping and detecting a particle beam.

It is a further object of the invention to provide an improved method and apparatus for shaping and detecting a particle beam without the use of sheath air.

It is yet another object of the invention to provide an improved method and apparatus for shaping and detecting a particle beam drawn from an aerosol at a relatively low pressure and having relatively small particles.

These and other objects are provided, according to the invention, by an apparatus for shaping an aerosol beam including a prefocusing element and a primary focusing element disposed within a tube or other lateral confining means. The prefocusing element receives the aerosol and preferentially expands the aerosol beam such that the lighter gas diverges laterally relatively rapidly while the heavier particles diverge laterally relatively slowly. The tube laterally confines the rapidly expanding gas such that the primary focusing element converges the gas back upon the particle beam to further narrow the particle beam.

A detector may be located downstream of the primary focusing means to sense the particles impinging thereon. A particle separation means is preferably interposed between the primary focusing element and the detector to remove a majority of the gas while allowing the majority of the particles to pass therethrough. The particles may be electrically charged and deflected prior to their detection such that the particles' relative masses may be determined by the detection means.

The prefocusing means has an orifice therethrough and is preferably a constriction and more preferably a nozzle, such as a converging conical nozzle, a capillary tube or a thin plate having an orifice therethrough. The tube has a relatively large diameter in comparison to the orifice defined by the prefocusing means, but is sufficiently small to laterally confine to rapidly expanding gas. The tube preferably has only a single inlet and a single outlet.

The primary focusing means is preferably in a spaced apart relation from the prefocusing means and has an orifice therethrough having a diameter which is relatively small in comparison to the inner diameter of the tube. The primary focusing means is preferably a constriction and more preferably a nozzle, such as a converging conical nozzle, a capillary tube or a thin plate having an orifice therethrough.

In operation, particles and gas from the aerosol beam source are drawn through the aerosol beam shaping apparatus by a pressure differential established between the relatively high pressure aerosol beam source and the relatively low pressure environment downstream of the primary focusing means. The aerosol beam is preferentially expanded laterally by the combination of the prefocusing means and the tube such that the gas expands relatively rapidly while the particles initially converge to a focal point prior to expanding relatively slowly.

The rapidly expanding gas is subsequently laterally confined by the tube which restricts the expansion of the gas. The laterally confined gas is thereinafter converged upon the slowly expanding particle beam to narrow the diameter of the beam of particles. This convergence of the gas is preferably accomplished by the primary focusing means in conjunction with the tube. Upon approaching the primary focusing means, the gas is forced inward toward the centerline of the tube, thereby reducing the cross-sectional area of the particle beam.

In conjunction with the particle beam shaping apparatus, a detection means and its associated particle excitation means may be utilized to sense the particles impinging thereon. The particle excitation means imparts an electrical charge to the particles prior to their detection. The electrical charge may be imparted by the particle excitation means photoelectrically, or more preferably electrically. The particle excitation means preferably produces a substantially planar sheet of electrons oriented substantially parallel to the longitudinal axis of propagation of the narrowed particle beam so as to intersect and electrically charge the narrowed particle beam. The particle excitation means is preferably an electron gun. The detection means, preferably an electron multiplier, a scintillation type detector or a Faraday cup detector, and most preferably a Faraday cup detector, can sense the electrical charge of the impinging particles and, based upon the amount of charge accumulated, determine the number of particles in the original aerosol sample.

Interposed between the primary focusing means and the particle excitation means is preferably a particle separation means for allowing the narrowed beam of particles to pass therethrough while removing a majority of the rapidly diverging gas. The particle separation means, preferably a skimmer, is positioned downstream of and spaced apart from a primary focusing means to allow preferential divergence therebetween such that the narrow particle beam initially converges to a focal point prior to diverging laterally relatively slowly and thus is passed through the orifice defined in the particle separation means while the lighter gas expands laterally relatively rapidly and is redirected by the particle separation means. The particle separation means is preferably located at the focal point of the particle beam to increase the transmission efficiency of the particles therethrough.

In addition, the particle beam shaping apparatus preferably includes particle deflection means downstream of the particle excitation means for deflecting each particle laterally by an amount inversely related to its mass. By detecting the position at which the particles impinge upon the detection means, the mass of the particles may be calculated therefrom. The particle deflection means preferably includes first and second oppositely-disposed deflection plates between which an electric field is established and through which the charged particle beam passes.

Electron and light ion deflection means are preferably downstream of the particle excitation means for removing any electrons not associated a particle as well as any electrically charged gas prior to their detection. The electron and light ion deflection means may establish a magnetic field, or more preferably an electric field for removing the electrons and light ions. The electron and light ion deflection means preferably includes first and second oppositely-disposed deflection plates between which an electric field is established and through which the charged particle beam passes.

The particle beam shaping method and apparatus of this invention allows sampling of environments at pressures less than 20 torr and produces a particle beam from which particles less than 0.1 um in diameter may be detected, which to the best of the inventor's knowledge has not heretofore been possible. In addition, the particle beam shaping method and apparatus eliminates the need for sheath air and its resulting production, control and contamination problems.

DESCRIPTION OF A PREFERRED EMBODIMENT

The present invention now will be described more fully hereinafter with reference to the accompanying drawings, in which a preferred embodiment of the invention is shown. This invention may, however, be embodied in many different forms and should not be construed as limited to the embodiments set forth herein; rather, this embodiment is provided so that this disclosure will be thorough and complete, and will fully convey the scope of the invention to those skilled in the art. Like numbers refer to like elements throughout.

Figure 1:
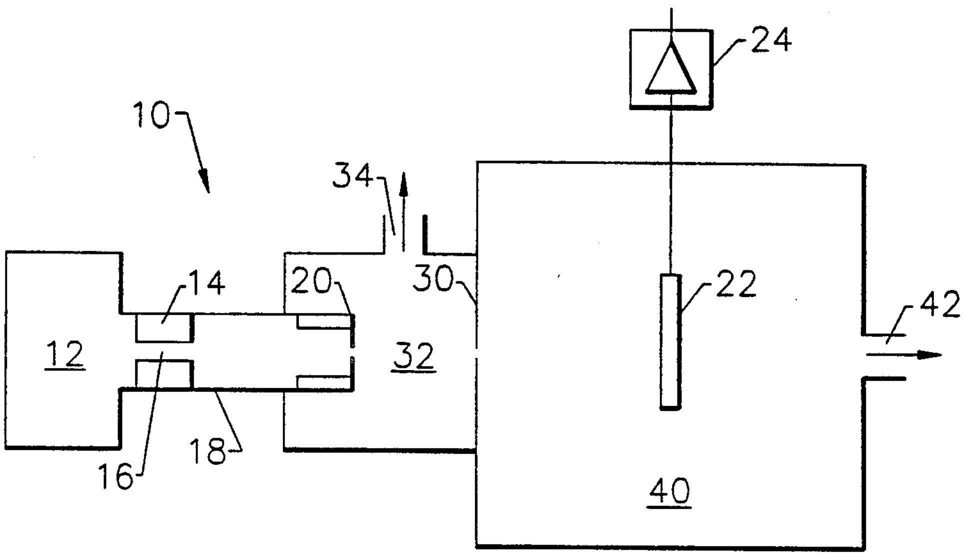
FIG. 1 is a schematic, cross-sectional view of a particle beam shaping and detecting apparatus according to the present invention.

Referring now to FIG. 1, an apparatus for shaping an aerosol beam according to the present invention is illustrated. The aerosol beam shaping apparatus 10 receives aerosol from an aerosol beam source 12 in which particles are mixed with a gas. The particles are relatively heavy in comparison to the lighter gas. Typically, the aerosol beam source 12 is a sample of particles suspended in a gas, such as that present during a microelectronic device processing step, in which the number and size, if desired, of the particles present are to be determined.

The aerosol beam shaping apparatus 10 includes a prefocusing means 14 for receiving the aerosol beam. The prefocusing means 14 is preferably a constriction and more preferably a capillary tube 50, a converging conical nozzle 52, a thin plate 54 having an orifice defined therethrough; or either a converging conical nozzle or a capillary tube with a thin plate 56 having an orifice therein disposed downstream of and adjacent thereto as illustrated in FIGS. 3A-3D. As shown in FIG. 1, the orifice 16 in the prefocusing means 14 defines the aerosol beam because the received aerosol is confined to passing through the orifice 16. The aerosol beam flow through the prefocusing means 14 is preferably subsonic such that there is only a relatively small pressure drop across the prefocusing means 14.

Figure 2:
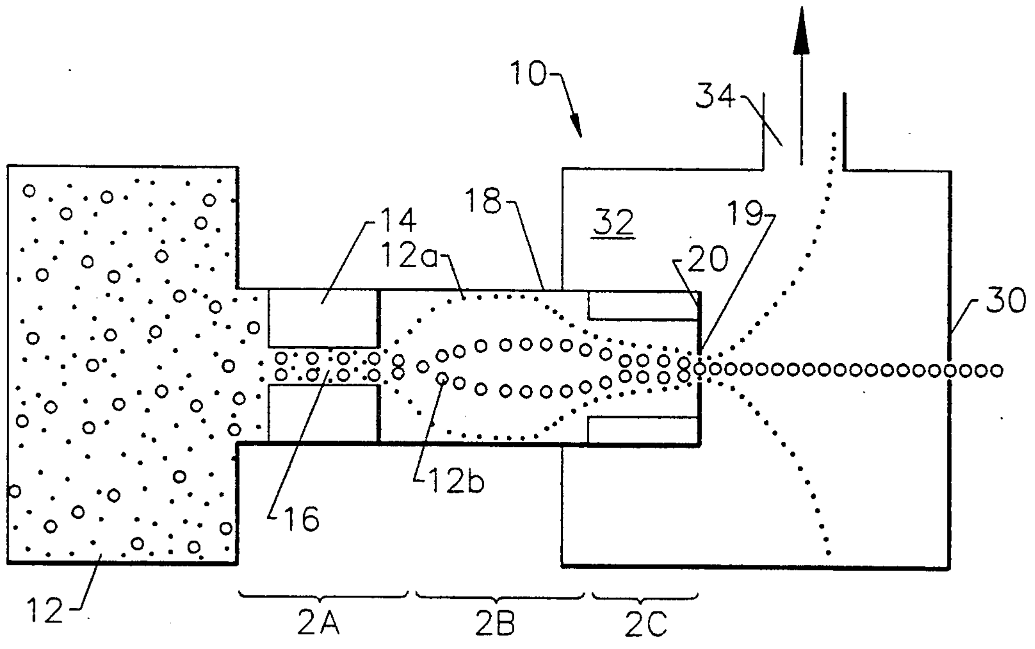
FIG. 2 is a cross-sectional view of the paths of particles and gas in a particle beam shaping apparatus according to the present invention.
Figure 3A:
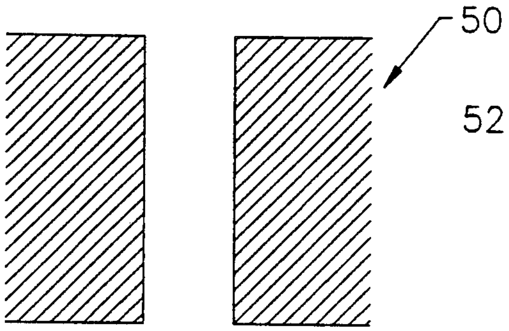
FIGS. 3A-3D are cross-sectional views of exemplary prefocusing and primary focusing elements utilized by a particle beam shaping apparatus of the present invention.
Figure 3B:
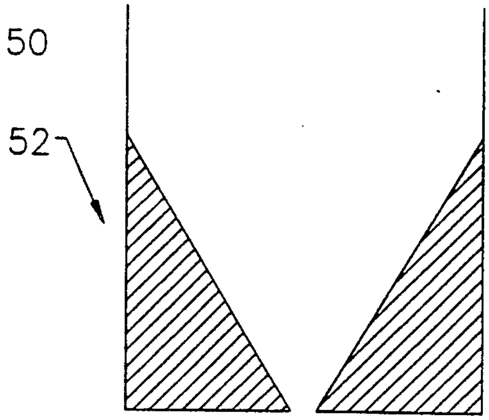
Figure 3C:
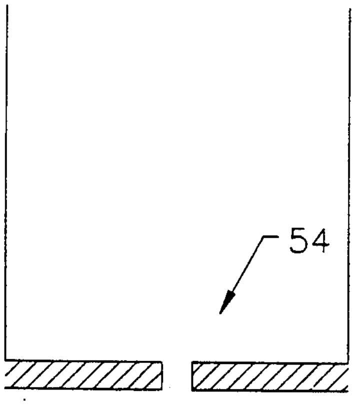
Figure 3D:
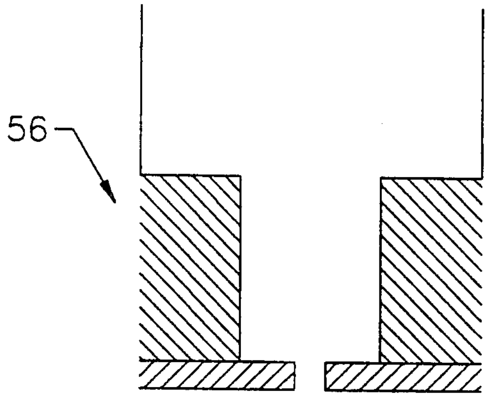

As illustrated by FIG. 2, the prefocusing means 14 produces a relatively rapid lateral expansion of the gas **12*a* emerging therefrom while the particles 12*b* initially converge to a focal point prior to expanding laterally relatively slowly. This preferential lateral expansion of the aerosol, shown in region 2A of FIG. 2, is due to the larger inertia of the particles 12*b* in comparison to the gas 12*a*. While both the gas 12*a* and the particles 12*b* are traveling at substantially the same velocity, the mass of the particles 12*b* is substantially greater than that of the gas 12*a* so as to give the particles 12*b* a substantially greater inertia than that of the gas 12*a*. With larger inertia, the particles 12*b* diverge less from the longitudinal axis of propagation established by the prefocusing means 14 in comparison to the lighter gas 12*a*** which has less inertia and thus diverges more rapidly from the longitudinal axis.

The aerosol beam shaping apparatus 10 includes a tube 18 or other lateral confining means for laterally confining the rapidly expanding gas emerging from the prefocusing means 14 as shown in region 2B of FIG. 2. The prefocusing means 14 is preferably disposed within the tube 18 such that the orifice 16 of the prefocusing means 14 has a substantially smaller diameter than the inner diameter of the tube 18.

As shown in region 2C of FIG. 2, primary focusing means 20 converges the gas **12*a*, Which has been laterally confined by the tube 18, back upon the slowly particles 12*b* to further narrow the cross-sectional area of the particle beam. Preferably, the primary focusing means 20 is disposed within the tube 18 downstream of and spaced apart from the prefocusing means 14 such that the laterally confined gas 12*a* is forced, by the interface of the tube 18 and the primary focusing means 20, back upon the longitudinal beam of particles 12*b*. The primary focusing means 20 has an orifice 19 therethrough having a diameter substantially smaller than the inner diameter of the tube 18. As illustrated in FIGS. 3A-3D, the primary focusing means 20 is preferably a constriction and more preferably a capillary tube 50; a converging conical nozzle 52; a thin plate 54 having an orifice therein; or either a converging conical nozzle or a capillary tube with a thin plate 56 having an orifice therein disposed downstream of and adjacent thereto. The aerosol beam preferably flows supersonically through the primary focusing means 20 such that the particles acquire relatively large inertia and therefore, following an initial convergence through a focal point, laterally diverge relatively slowly downstream of the primary focusing means 20**.

The aerosol beam shaping apparatus 10 may produce a particle beam for use in detecting the number and size of particles in the aerosol beam source 12. To detect the number or presence of particles in the thus-formed particle beam, the aerosol beam shaping apparatus 10 is used in conjunction with a detection means 22 positioned downstream of the primary focusing means 20 as illustrated in FIGS. 1 and 4.

While various particle detection methods may be utilized, it is preferable to electrically charge the particles and thereinafter detect the charged particles with the detection means 22. Therefore, the detection means 22 is preferably an electron multiplier, a scintillation type detector or a Faraday cup detector, and most preferably a Faraday cup detector comprising a metal plate or collector cup to which an electrometer 24 is connected. The detection means 22 measures the electric current associated with the charged particles impacting the metal plate. For most efficient detection, a thin layer of electrically conducting vacuum grease should be applied to the metal plate of the Faraday cup detector in order to prevent particles from bouncing off the metal plate and not being detected.

Figure 4:
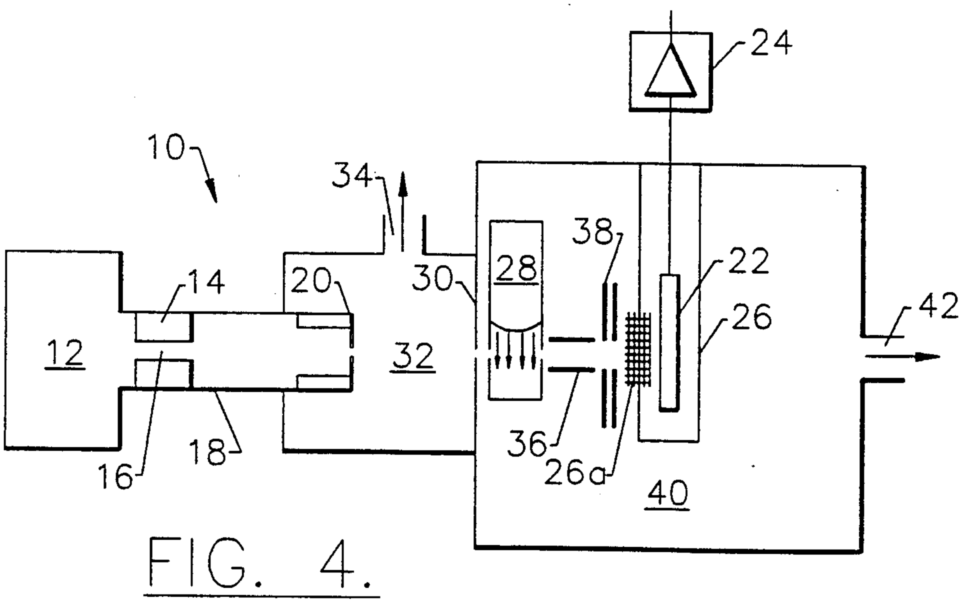
FIG. 4 is a schematic, cross-sectional view of a particle beam shaping and detecting apparatus including detection means according to the present invention.

As shown in FIG. 4, the detection means 22 is preferably disposed within a grounded metal housing 26 to shield the detection means 22 from electric fields and stray electrons. A first face of the metal housing 26, oriented upstream to receive the particle beam, includes a grounded wire mesh grid 26a for allowing particles to pass therethrough in order to be detected.

In order to electrically excite the particles prior to their detection, a particle excitation means 28 is preferably positioned downstream of the primary focusing means 20 as shown in FIG. 4. The particle excitation means may excite the particles photoelectrically, or more preferably electrically. The particle excitation means 28 preferably produces a substantially planar sheet of electrons oriented substantially parallel to the longitudinal axis of the narrowed particle beam so as to intersect the particle beam and impart an electrical charge to the particles. By utilizing a planar sheet of electrons, the particle excitation means 28 significantly increases the number of interactions between particles and electrons in comparison to a cylindrical electron stream. By increasing the number of interactions between particles and electrons, the number of charged particles and thus the charging efficiency of the particle beam is increased.

In addition, electron and light ion deflection means 38 are preferably associated with and downstream of the particle excitations means 28. While the electrons and light ions, such as electrically-charged gas molecules, may be deflected with a magnetic field, an electric field is preferably established by the electron and light ion deflection means 38. In particular, the electron and light ion deflection means 38 are preferably a pair of electron deflection plates having an electric field established therebetween. The electron deflection plates are positioned such that the charged particle beam flows therebetween and stray electrons, not associated with a particle, as well as light ions are deflected or removed from the particle beam. The deflected electrons and light ions are therefore not subsequently detected.

Referring again to FIGS. 1 and 4, a particle separation means 30, preferably a skimmer, is preferably interposed between the primary focusing means 20 and the particle beam excitation means 28. The skimmer 30, preferably a thin plate having an orifice therein, is preferably disposed at a first end of a chamber 32 with the primary focusing means 20 located at a second end of the chamber 32. The skimmer 30 is spaced apart from the primary focusing means 20 to allow the particles and gas emerging from the primary focusing means 20 to preferentially expand once again such that the gas expands laterally relatively rapidly while the particles initially converge to a focal point prior to expanding laterally relatively slowly. The particle separation means 30 is preferably located at the particles' focal point to increase the particles' transmission efficiency therethrough.

The chamber 32 also has a vacuum port 34 such that the rapidly laterally expanding gas is drawn through the vacuum port 34 while the slowly expanding particle beam passes through the orifice defined by the skimmer 30. While the design of the particle beam shaping apparatus will depend upon its application, the pressure within chamber 32 is generally approximately ten percent of the pressure within the tube 18. In addition, the focal point of the particle beam, at which the skimmer 30 is preferably located, is generally located a distance approximately equal to one to fifty times the orifice diameter of the primary focusing means 20. The orifice of the skimmer 30 has a diameter approximately one-half that of the orifice of the primary focusing means 20. This orifice sizing provides that the particle beam, but only a minimal amount of gas, is passed through the skimmer 30.

If the relative masses of the particles, in addition to the number of particles is to be determined, particle deflection means 36, preferably a pair of particle deflection plates, are interposed between the particle excitation means 28 and the detection means 22. The particle deflection plates have different electric potentials applied thereto to generate an electric field therebetween. The particle deflection plates are positioned such that the charged particle beam passes therebetween. The particles are deflected by the electrical force resulting from the interaction of the electric field established by the particle deflection plates and the electric charge associated with the particle. By measuring the amount of deflection of the particles at varying electric field strengths, the particles' relative masses may be calculated therefrom.

A detection chamber 40 preferably houses the particle excitation means 28; the particle deflection means 36, if any; the electron deflection means 38; and the detection means 22. The detection chamber 40 has a vacuum port 42 such that a pressure differential may be established between the relatively lower pressure of the detection chamber 40 and the relatively higher pressure of the aerosol beam source 12. The pressure differential draws the aerosol beam from the aerosol beam source 12 to the detection chamber 40.

The shapes and diameters of the orifices defined by the primary focusing means 20 and the prefocusing means 14, as well as the diameter of the tube 18, may be varied to alter the shape of the particle beam. In addition, the shape of the particle beam may be altered by varying the length of either the prefocusing means 14 or the primary focusing means 20; or the longitudinal distance therebetween.

Typically, the combination of the tube 18 and the primary focusing means 20 principally determines the focal length of the particle beam With longer focal lengths typically produced, for primary focusing means 20 of a fixed size, by a tube having a smaller internal diameter. The prefocusing means 14 also typically narrows the particle beam and thus, in conjunction with the primary focusing means 20, allows for relatively long focal lengths without reducing the diameter of the orifice of the primary focusing means 20. Additionally, the use of a prefocusing means 14 provides for increased particle transmission efficiency, particularly for particles having relatively large diameters, less geometric aberration and a more narrow particle beam than the use of a primary focusing means alone.

The particle beam shaping method and apparatus of this invention allows sampling of environments having pressures less than about 20 torr, such as 0.1 torr, and produces a particle beam from which particles less than about 0.1 um, such as 0.01 um, in diameter may be detected which to the best of the inventors' knowledge has not been previously accomplished. In addition, for applications requiring a relatively small particle beam, the particle beam shaping method and apparatus may provide a particle beam having a smaller diameter than that of the primary focusing means 20 over longitudinal distances of approximately twenty to thirty times the diameter of the primary focusing means 20.

In the drawings and specification, there have been disclosed typical preferred embodiments of the invention and, although specific terms are employed, the terms are used in a generic and descriptive sense only and not for purposes of limitation, the scope of the invention being set forth in the following claims.

That which is claimed is:

1. An apparatus for shaping an aerosol beam having particles suspended in a gas, comprising:

prefocusing means for receiving an aerosol beam and for producing relatively rapid lateral expansion of said gas emerging therefrom and relatively slow lateral expansion of said particles emerging therefrom;

means for laterally confining said rapidly expanding gas emerging from said prefocusing means; and primary focusing means downstream of said prefocusing means for converging said laterally confined gas back upon said slowly expanding particles to narrow said slowly expanding beam of particles.

2. An apparatus for shaping an aerosol beam according to claim 1 wherein said lateral confining means is a tube and said prefocusing means has an orifice therethrough, said orifice having an inner diameter substantially smaller than the inner diameter of said tube.

3. An apparatus for shaping an aerosol beam according to claim 2 wherein said prefocusing means is selected from the group consisting of at least one of a converging conical nozzle, a capillary tube and a thin plate having an orifice therethrough.

4. An apparatus for shaping an aerosol beam according to claim 1 wherein said lateral confining means is a tube and said primary focusing means has an orifice therethrough, said orifice having an inner diameter substantially smaller than the inner diameter of said tube.

5. An apparatus for shaping an aerosol beam according to claim 2 wherein said primary focusing means is selected from the group consisting of at least one of a converging conical nozzle, a capillary tube and a thin plate having an orifice therethrough.

6. An apparatus for shaping an aerosol beam according to claim 1 further comprising an aerosol beam source operably connected to said prefocusing means.

7. An apparatus for shaping a beam of particles according to claim 1 further comprising separation means, interposed between said primary focusing means and said detection means, for allowing said narrowed particle beam to pass therethrough and for redirecting said gas.

8. An apparatus for shaping a beam of particles according to claim 7 wherein said separation means is a thin plate having an orifice therethrough.

9. An apparatus for shaping an aerosol beam according to claim 1 further comprising detection means downstream of said primary focusing means for sensing said particles impinging thereon.

10. An apparatus for shaping a beam of particles according to claim 9, further comprising particle excitation means, interposed between said separation means and said detection means, for imparting an electrical charge to said narrowed particle beam.

11. An apparatus for shaping a beam of particles according to claim 10 wherein said particle excitation means produces a substantially planar sheet of electrons, said substantially planar sheet of electrons being oriented substantially parallel to the longitudinal axis of propagation of said narrowed particle beam and intersecting said narrowed particle beam.

12. An apparatus for shaping a beam of particles according to claim 11 wherein said particle excitation means is an electron gun.

13. An apparatus for shaping a beam of particles according to claim 10 further comprising electron and light ion deflection means, interposed between said particle excitation means and said detection means, for removing substantially all light ions and electrons not associated with a particle from said charged particle beam.

14. An apparatus for shaping a beam of particles according to claim 13 wherein said electron and light ion deflection means comprises a first electron deflection plate and a second electron deflection plate spaced apart from said first electron deflection plate such that an electrical field may be established therebetween, said first and second electron deflection plates positioned such that said charged particle beam passes therebetween.

15. An apparatus for shaping a beam of particles according to claim 10 further comprising particle deflection means, interposed between said particle excitation means and said detection means, for laterally deflecting said particles of said charged particle beam wherein the amount of said lateral deflection of each charged particle depends upon the mass of said particle.

16. An apparatus for shaping a beam of particles according to claim 15 wherein said particle deflection means comprises a first particle deflection plate and a second particle deflection plate spaced apart from said first particle deflection plate such that an electrical field may be established therebetween, said first and second particle deflection plates positioned such that said charged particle beam passes therebetween.

17. An apparatus for shaping a beam of particles according to claim 7 wherein said detection means comprises a Faraday cup detector and an electrometer operably connected to said Faraday cup detector for measuring the electrical charge accumulated on said Faraday cup detector.

18. An apparatus for shaping an aerosol beam having particles suspended in a gas, comprising:

a tube having only a single inlet, for receiving said aerosol beam of particles and gas, and only a single outlet;

at least one first constriction disposed within said tube for constricting said particles and gas entering therein and for producing relatively rapid lateral expansion of said gas emerging therefrom and relatively slow lateral expansion of said particles emerging therefrom; and a least one second constriction disposed within said tube downstream of and spaced apart from said at least one first constriction for further constricting said slowly expanding particles and for directing said constricted particles to said single outlet of said tube.

19. An apparatus for shaping an aerosol beam having particles suspended in a gas according to claim 18 wherein said at least one first constriction has an orifice therethrough, said orifice having an inner diameter substantially smaller than the inner diameter of said tube.

20. An apparatus for shaping an aerosol beam having particles suspended in a gas according to claim 18 wherein said at least one second constriction has an orifice therethrough said orifice having an inner diameter substantially smaller than the inner diameter of said tube.

21. An apparatus for shaping an aerosol beam having particles suspended in a gas according to claim 18 wherein said at least one first constriction is a first capillary tube having an inner diameter substantially smaller than the inner diameter of said tube and wherein said at least one second constriction is a second capillary tube upstream of and adjacent to a thin plate having an orifice therethrough, said second capillary tube having an inner diameter substantially smaller than the inner diameter of said tube and said orifice defined by said thin plate having a diameter smaller than said inner diameter of said second capillary tube.

22. An apparatus for sensing a beam of particles, comprising:

prefocusing means for receiving said beam of particles and for producing relatively rapid lateral expansion of said gas emerging therefrom and relatively slow lateral expansion of said particles emerging therefrom;

means for laterally confining said rapidly expanding gas emerging from said prefocusing means;

primary focusing means downstream of said prefocusing means for converging said laterally confined gas back upon said slowly expanding particles to narrow said slowly expanding beam of particles; and detection means downstream of said primary focusing means for sensing said particles impinging thereon.

23. An apparatus for sensing a beam of particles according to claim 22 further comprising separation means, interposed between said primary focusing means and said detection means, for allowing said narrowed particle beam to pass therethrough and for redirecting said gas.

24. An apparatus for sensing a beam of particles according to claim 23 wherein said separation means is a thin plate having an orifice therethrough.

25. An apparatus for sensing a beam of particles according to claim 23, further comprising particle excitation means, interposed between said separation means and said detection means, for imparting an electrical charge to said narrowed particle beam.

26. An apparatus for sensing a beam of particles according to claim 25 wherein said particle excitation means produces a substantially planar sheet of electrons, said substantially planar sheet of electrons being oriented substantially parallel to the longitudinal axis of propagation of said narrowed particle beam and intersecting said narrowed particle beam.

27. An apparatus for sensing a beam of particles according to claim 26 wherein said particle excitation means is an electron gun.

28. An apparatus for sensing a beam of particles according to claim 25 further comprising electron and light ion deflection means, interposed between said particle excitation means and said detection means, for removing substantially all light ions and electrons not associated with a particle from said charged particle beam.

29. An apparatus for sensing a beam of particles according to claim 28 wherein said electron and light ion deflection means comprises a first electron deflection plate and a second electron deflection plate spaced apart from said first electron deflection plate such that an electrical field may be established therebetween, said first and second electron deflection plates positioned such that said charged particle beam passes therebetween.

30. An apparatus for sensing a beam of particles according to claim 25 further comprising particle deflection means, interposed between said particle excitation means and said detection means, for laterally deflecting said particles of said charged particle beam wherein the amount of said lateral deflection of each charged particle depends upon the mass of said particle.

31. An apparatus for sensing a beam of particles according to claim 30 wherein said particle deflection means comprises a first particle deflection plate and a second particle deflection plate spaced apart from said first particle deflection plate such that an electrical field may be established therebetween, said first and second particle deflection plates positioned such that said charged particle beam passes therebetween.

32. An apparatus for sensing a beam of particles according to claim 22 wherein said detection means comprises a Faraday cup detector and an electrometer operably connected to said Faraday cup detector for measuring the electrical charge accumulated on said Faraday cup detector.

33. A method for shaping an aerosol beam having particles suspended in a gas, comprising the steps of:

preferentially expanding said aerosol beam laterally such that said gas expands relatively rapidly and said particles expand relatively slowly;

laterally confining said rapidly expanding gas; and converging said laterally confined gas upon said slowly expanding particles to narrow said slowly expanding particle beam.

34. A method for shaping an aerosol beam having particles suspended in a gas according to claim 33, further comprising the step of detecting said particles in said narrowed particle beam.

35. A method for shaping an aerosol beam having particles suspended in a gas according to claim 34, further comprising the steps of:

preferentially expanding said aerosol beam laterally, following said converging step, such that said gas expands relatively rapidly and said narrowed particle beam expands relatively slowly; and separating said rapidly expanding gas from said narrowed particle beam prior to detecting said particles.

36. A method for shaping an aerosol beam having particles suspended in a gas according to claim 34, further comprising the step of exciting said particles of said narrowed particle beam, prior to said detecting step, by impinging electrons thereon.

37. A method for shaping an aerosol beam having particles suspended in a gas according to claim 36, further comprising the step of removing substantially all light ions and electrons and light ions not associated with a particle of said charged particle beam prior to said detecting step.

38. A method for shaping an aerosol beam having particles suspended in a gas according to claim 36, further comprising the step of laterally deflecting. said charged particles of said charged particle beam such that the amount of lateral deflection of each charged particle depends upon with the mass of each said particles prior to said detecting step.

* * * * *